United States Patent
Wang et al.

(10) Patent No.: US 10,669,223 B2
(45) Date of Patent: Jun. 2, 2020

(54) METHOD FOR SYNTHESIZING 4-(HYDROXYMETHYL)BENZOIC ACID BY USING P-XYLENE (PX) AS RAW MATERIAL

(71) Applicant: YUNNAN UNIVERSITY, Kunming (CN)

(72) Inventors: Jiaqiang Wang, Kunming (CN); Ying Li, Kunming (CN); Daomei Chen, Kunming (CN)

(73) Assignee: YUNNAN UNIVERSITY, Kunming (CN)

( * ) Notice: Subject to any disclaimer, the term of this patent is extended or adjusted under 35 U.S.C. 154(b) by 0 days.

(21) Appl. No.: 16/609,203

(22) PCT Filed: May 5, 2018

(86) PCT No.: PCT/CN2018/085754
§ 371 (c)(1),
(2) Date: Oct. 28, 2019

(87) PCT Pub. No.: WO2018/228081
PCT Pub. Date: Dec. 20, 2018

(65) Prior Publication Data
US 2020/0062685 A1    Feb. 27, 2020

(30) Foreign Application Priority Data
Jun. 15, 2017  (CN) .......................... 2017 1 0451197

(51) Int. Cl.
*C07C 51/285*     (2006.01)
*B01J 31/16*      (2006.01)
*C07C 65/01*      (2006.01)

(52) U.S. Cl.
CPC ......... *C07C 51/285* (2013.01); *B01J 31/1691* (2013.01); *C07C 65/01* (2013.01)

(58) Field of Classification Search
None
See application file for complete search history.

(56) References Cited

U.S. PATENT DOCUMENTS

| 9,328,050 B1 | 5/2016 | Boppana et al. | |
| 2003/0073206 A1* | 4/2003 | Bramucci | C12N 9/0071 435/137 |

FOREIGN PATENT DOCUMENTS

| CN | 107827730 A | 3/2018 |
| WO | 03014368 A2 | 2/2003 |

OTHER PUBLICATIONS

Samuel J. Fretz, et al. Birch Reductive Alkylation of Methyl m-(Hydroxymethyl) benzoate Derivatives and the Behavior of o- and p-(Hydroxymethyl) benzoates under Reductive Alkylation Conditions. The Journal of Organic Chemistry, 2012, 78(1), pp. 83-92.

(Continued)

*Primary Examiner* — Sudhakar Katakam
*Assistant Examiner* — Jennifer C Sawyer
(74) *Attorney, Agent, or Firm* — Bayramoglu Law Offices LLC

(57) ABSTRACT

A method for synthesizing 4-(Hydroxymethyl)benzoic acid using P-xylene (PX) as a raw material, including: dissolving PX in an organic solvent to undergo an oxidation reaction with an oxidizing agent under an action of an M-MOF catalyst; and after the oxidation reaction, performing a post-treatment to obtain the 4-(Hydroxymethyl)benzoic acid; wherein, the metal element M in the M-MOF catalyst is Fe, Cu, Cr, Mn, Cu/Fe, Cu/Cr, Cu/Mn, Fe/Mn, Cr/Fe or Cr/Mn. The by-product produced in the reaction process is little, the yield is high, and the separation is convenient. The acid-base neutralization is not required in the reaction process, reducing pollution. A one-step reaction is employed which has mild reaction conditions, short reaction time, low pollution and is convenient for industrialized mass produc- (Continued)

tion; and the obtained 4-(Hydroxymethyl)benzoic acid can be used for preparing medicines and liquid crystal materials having wide applications.

18 Claims, 6 Drawing Sheets

(56) References Cited

OTHER PUBLICATIONS

Sebastian, Imm, et al. Improved Ruthenium-Catalyzed Amination of Alcohols with Ammonia: Synthesis of Diamines and Amino Esters. Angewandte Chemie International Edition, 2011, 50(33), pp. 7599-7603.

Colin C. Seaton, et al. Making Benzamide Cocrystals with Benzoic Acids: The Influence of Chemical Structure. Crystal Growth & Design, 2011, 11(5), pp. 1502-1511.

Niranjan Kumar Namelikonda et al. Sulfo-click reaction via in situ generated thioacids and its application in kinetic target-guided synthesis. Chemical Communications, 2012, 48(10), pp. 1526-1528.

Michael B. Andrews, et al. Uranyl Hybrid Material Derived from In Situ Ligand Synthesis: Formation, Structure, and an Unusual Phase Transformation. Angewandte Chemie International Edition, 2012, 51(27), pp. 6631-6634.

Samuel Annen, et al. Catalytic Aerobic Dehydrogenative Coupling of Primary Alcohols and Water to Acids Promoted by a Rhodium(I) Amido N-Heterocyclic Carbene Complex. ChemCatChem, 2010, 2(10), pp. 1286-1295.

Li, Ying et al. One-Step Synthesis of 2, 5-Dihyrocyterephthalic Acid by the Oxidation of P-Xylene over M-MCM-41 (M=Fe, Fe/Cu, Cu) Catalysts, Chemical Engineering Journal, Aug. 3, 2016, vol. 306, pp. 777-783.

Xu, Lai, et al. Research Progress On Catalytic Oxidation of Styrene over Metal-Organic Frameworks, Guangdong Chemical Industry, Dec. 31, 2015, 42(12), pp. 75-76.

\* cited by examiner

METHOD FOR SYNTHESIZING 4-(HYDROXYMETHYL)BENZOIC ACID BY USING P-XYLENE (PX) AS RAW MATERIAL

CROSS REFERENCE TO RELATED APPLICATIONS

This application is the national phase entry of International Application No. PCT/CN2018/085754, filed on May 5, 2018, which is based upon and claims priority to Chinese Patent Application No. 201710451197.4, filed on Jun. 15, 2017, the entire contents of which are incorporated herein by reference.

TECHNICAL FIELD

The present invention belongs to the technical field of chemical synthesis of 4-(Hydroxymethyl)benzoic acid, and in particular to a method for synthesizing 4-(Hydroxymethyl)benzoic acid by using P-xylene (PX) as a raw material.

BACKGROUND

P-xylene (PX) is a key organic chemical raw material mainly employed in preparing important organic intermediates, such as terephthalic acid, etc., for producing polymers. The p-xylene has relatively abundant sources and a low price, which can be obtained by methods such as disproportionation of toluene, isomerization of xylene, aromatization of methanol, and reaction of 2,5-dimethylfuran with ethylene, etc. At present, a productive capacity of p-xylene is about 15 million tons/year in China. Therefore, it will greatly promote the development of p-xylene industry by expanding a development and utilization of downstream products of the p-xylene.

With the continuous recognition and broad application of oxygen-containing aromatic compounds, oxygen-containing organic compounds, such as terephthalic acid, 2,5-dihydroxyterephthalic acid, 4-(Hydroxymethyl)benzoic acid, etc., play more and more prominent roles in human production and living. These organic compounds are mainly used for synthesizing polymers, novel lithium batteries, drugs, etc. Although these oxides are widely used, the oxides such as 2,5-dihydroxyterephthalic acid, 4-(Hydroxymethyl)benzoic acid, etc. are rarely synthesized by a one-step oxidation using p-xylene which has a low price and abundant sources as a raw material, except that the terephthalic acid is obtained by an oxidation of the p-xylene.

In recent years, 4-(Hydroxymethyl)benzoic acid has been widely used in the synthesis and application of drugs, pharmaceutical intermediates, photocatalytic materials and optoelectronic materials (The Journal of organic chemistry, 2012, 78(1): 83-92; Angewandte Chemie International Edition, 2011, 50(33): 7599-7603; Crystal Growth & Design, 2011, 11(5): 1502-1511; Chemical Communications, 2012, 48(10): 1526-1528; Angewandte Chemie International Edition, 2012, 51(27): 6631-6634), and 4-(Hydroxymethyl) benzoic acid is considered to be an extremely high-value chemical intermediate.

Although the application of 4-(Hydroxymethyl)benzoic acid has attracted widespread attention, synthesis methods of 4-(Hydroxymethyl)benzoic acid have no big breakthrough. Conventional synthesis methods are as follows. 4-(Hydroxymethyl)benzoic acid is obtained by reacting 4-methylbenzoic acid with bromine to form 4-bromomethylbenzoic acid, and then hydrolyzing the 4-bromomethylbenzoic acid (FIG. 1, A). Alternatively, 4-(Hydroxymethyl) benzoic acid is obtained by selectively oxidizing 1,4-benzenedimethanol using a catalyst (FIG. 1, B) (ChemCatChem, 2010, 2(10): 1286-1295; U.S. Pat. No. 9,328,050B1). For the above two methods, many reaction steps are needed. It is necessary to first obtain 4-methylbenzoic acid or 1,4-dicarboxybenzene by methods such as oxidizing p-xylene, etc., and then next reaction can be performed, which causes a lot of by-products. Moreover, bromides produced in the reaction cause corrosion to devices or expensive catalysts are used in the above methods, which deviates from the concept of green chemistry. Therefore, a more convenient, efficient, and inexpensive synthesis method is needed for producing large amounts of 4-(Hydroxymethyl)benzoic acid.

In view of the above problems, it is quite necessary to develop a milder and greener method for synthesizing 4-(Hydroxymethyl)benzoic acid. M. G. Bramucci et al. obtain 4-(Hydroxymethyl)benzoic acid by using a xylene monooxygenase as a catalyst to perform a biomimetic catalytic oxidation on p-xylene (U.S. Pat. No. 20030073206A1). However, this method has problems such as long reaction time, low yield, and complicated cultivation of biocatalyst.

SUMMARY

In view of the drawbacks of multiple reaction steps, harsh reaction conditions, long reaction time, low yield, pollution and the like in the current process for synthesizing 4-(Hydroxymethyl)benzoic acid, the present invention provides a method for synthesizing 4-(Hydroxymethyl)benzoic acid by using PX as a raw material, the present invention can synthesize 4-(Hydroxymethyl)benzoic acid in one step.

The technical solution of the present invention is as follows: a method for synthesizing 4-(Hydroxymethyl)benzoic acid using PX as a raw material, including: dissolving PX in an organic solvent to undergo an oxidation reaction with an oxidizing agent under an action of an metal element based metal-organic framework (M-MOF) catalyst; and after the oxidation reaction, performing a post-treatment to obtain the 4-(Hydroxymethyl)benzoic acid; wherein, a metal element M in the M-MOF catalyst is Fe, Cu, Cr, Mn, Cu/Fe, Cu/Cr, Cu/Mn, Fe/Mn, Cr/Fe or Cr/Mn; organic ligands in the M-MOF catalyst are different, including terephthalic acid and trimesic acid.

Preferably, the metal element M in the M-MOF catalyst is Cu, Cu/Cr, Cu/Mn or Fe/Mn.

The organic solvent is at least one selected from the group consisting of methanol, ethanol, acetonitrile, acetone, acetic acid, ethyl acetate, and cyclohexane.

Preferably, the organic solvent is at least one selected from the group consisting of acetonitrile, acetone, and acetic acid.

The oxidizing agent is at least one selected from the group consisting of $O_2$, air, hydrogen peroxide, $KHSO_5$, t-butyl hydroperoxide, $O_3$ and $N_2O$.

Preferably, the oxidizing agent is at least one selected from the group consisting of 20%-40% hydrogen peroxide, t-butyl hydroperoxide, $O_3$ and $N_2O$.

Further preferably, the oxidizing agent is 20%-40% hydrogen peroxide and/or t-butyl hydroperoxide, and a molar ratio of the PX to the oxidizing agent is 1:(3-10). When $H_2O_2$, $KHSO_5$ or the t-butyl hydroperoxide is used as the oxidizing agent, the oxidizing agent is added to a reaction solution in an amount of 1.5 times effective oxygen.

In the present invention, with a cooperation of the preferred catalyst, the preferred solvent and the preferred oxidizing agent, a yield of the 4-(Hydroxymethyl)benzoic acid can reach equal to or more than 80%, even up to 90% or higher in some embodiments. Less impurity and higher yield are achieved, and the present invention is suitable for industrial synthesis of 4-(Hydroxymethyl)benzoic acid.

A volume ratio of the PX to the organic solvent is 1:(1-100), and preferably, the volume ratio of the PX to the organic solvent is 1:(5-30).

In the oxidation reaction, a reaction temperature is 10-120° C. and a reaction time is 1-24 hours; different reaction temperatures or different amounts of reaction substrates lead to different reaction time.

A mass ratio of the PX to the M-MOF catalyst is 1:(1.5-3).

A mass ratio of the metal element M to a MOF carrier in the M-MOF catalyst is 1:(10-100).

The post-treatment includes filtering the reaction solution, removing the solvent from a filtrate, and then performing a column chromatography or recrystallization, thereby obtaining the 4-(Hydroxymethyl)benzoic acid.

The present invention has the following features: in the present invention, the M-MOF catalyst is used to obtain the desired product, 4-(Hydroxymethyl)benzoic acid, by a one-step oxidation reaction. The catalyst is capable of acting on the PX for selective oxidation reaction to obtain the 4-(Hydroxymethyl)benzoic acid. In the present invention, there are few by-products such as p-methylbenzyl alcohol, 4-methylbenzoic acid, etc., because the p-methylbenzyl alcohol is easily coordinated with the metal ion at the center of the M-MOF catalyst. The compound after being coordinated is further oxidized to the 4-methylbenzoic acid by the action of the oxidizing agent, and then the 4-methylbenzoic acid adsorbed on the active site of the catalyst is oxidized again to the 4-(Hydroxymethyl)benzoic acid. In the present invention, there is less terephthalic acid, because after the p-xylene is oxidized to the 4-(Hydroxymethyl)benzoic acid under the action of the M-MOF catalyst, the 4-(Hydroxymethyl)benzoic acid is desorbed from the surface of the catalyst, thereby effectively preventing the 4-(Hydroxymethyl)benzoic acid from further being oxidized into the terephthalic acid.

Compared with the prior art, the present invention has the following advantages: the raw material required in the present invention has abundant sources and a low price; the by-product produced in the reaction process is little, the yield is high, and the separation is convenient; the acid-base neutralization is not required in the reaction process, reducing the pollution; a one-step reaction is employed in the present invention, which has mild reaction conditions, short reaction time, low pollution, and is convenient for industrialized mass production; and the obtained 4-(Hydroxymethyl)benzoic acid can be used for preparing medicines, liquid crystal materials, etc., having wide applications and relatively high value.

DETAILED DESCRIPTION OF THE EMBODIMENTS

Figure 1:
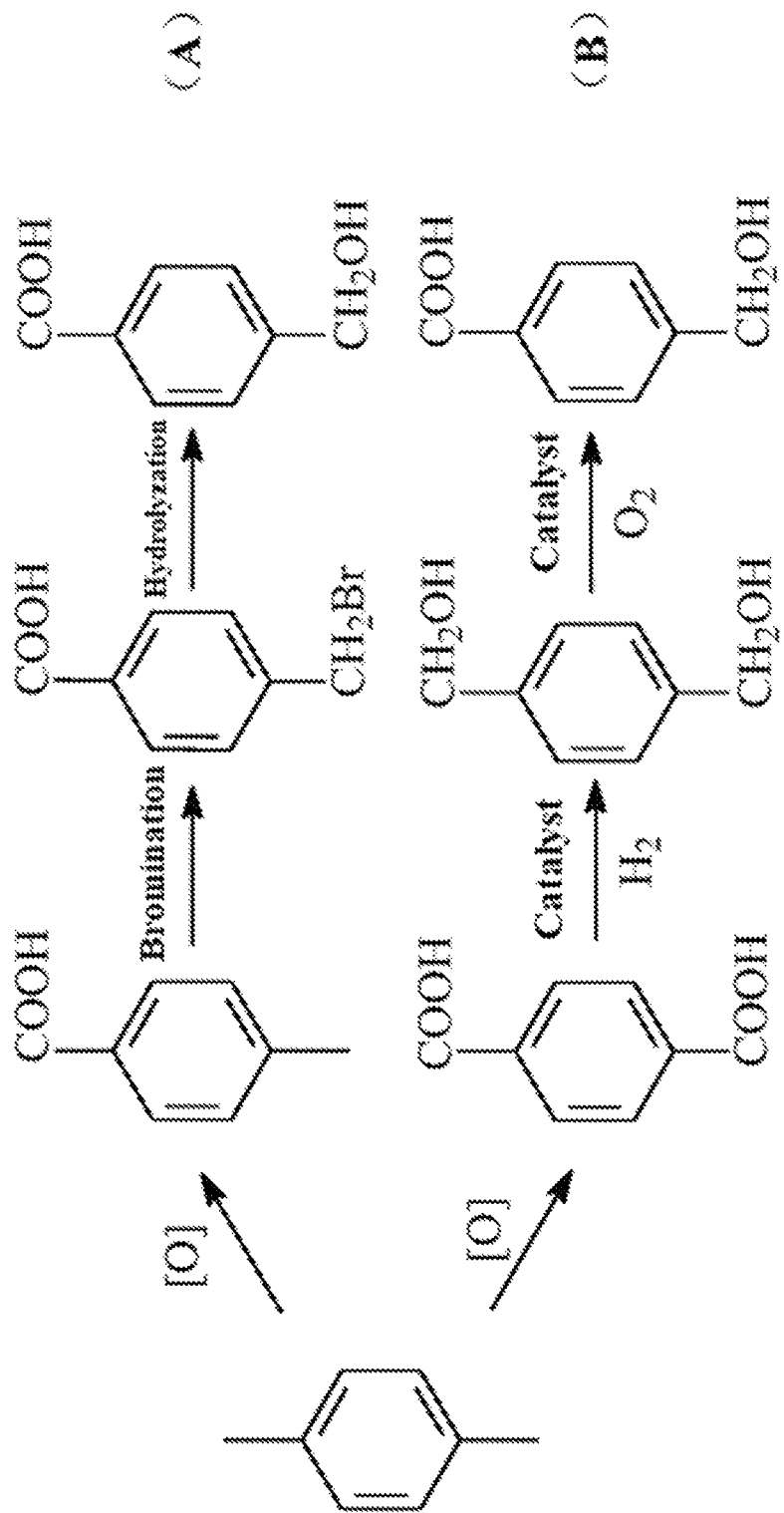
FIG. 1 is a diagram showing an existing synthetic route of 4-(Hydroxymethyl)benzoic acid.
Figure 2:
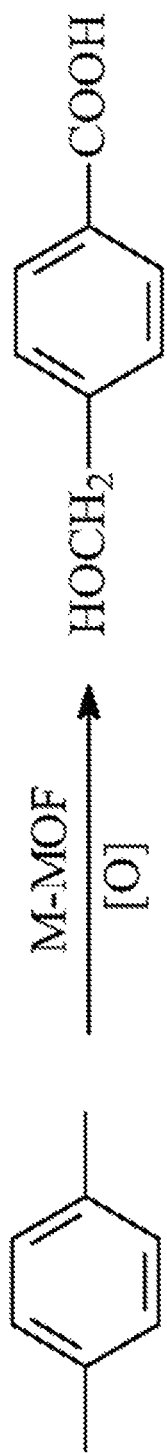
FIG. 2 is a diagram showing a synthetic route of 4-(Hydroxymethyl)benzoic acid in the present invention.

The technical solution of the present invention will be further described in detail below with the reference to the accompanying drawings and specific embodiments. A synthetic route of the present invention is shown in FIG. 2. A density of p-xylene in the following embodiments is 0.86 g/cm$^3$.

A synthesis method of Fe-MOF is a hydrothermal method, including the following experimental steps. 0.675 g of FeCl$_3$·6H$_2$O and 260 mg of terephthalic acid are weighed and transfered into a reacting lining made of polytetrafluoroethylene, and 15 mL of a solvent (N,N-dimethylformamide (DMF)) is added. At normal temperature, the solution is stirred at a low speed to be clear and transparent, and transferred into a dryer. A temperature of the dryer is set to be 110° C. at which a reaction is performed for 20 hours. After the reaction was terminated, and the reaction kettle is naturally cooled, a suction filtration is carried out with DMF until a filtrate is colorless to obtain a brick red solid material, i.e., the Fe-MOF.

The experimental steps for synthesizing Mn/Fe-MOF are as follows: certain amounts of FeCl$_3$·6H$_2$O, terephthalic acid and Mn(NO)$_3$·4H$_2$O are dissolved in an appropriate amount of DMF, and transferred into a reacting lining made of polytetrafluoroethylene, a reaction is carried out at 110° C. for 20 hours, after the reaction kettle is naturally cooled, the product is washed with DMF to obtain the Mn/Fe-MOF.

Cu-MOF is a pore-channel framework material composed of a metal center Cu$^{2+}$ and an organic ligand 1,3,5-benzenetricarboxylic acid. The specific preparation process of the Cu-MOF used in this experiment is as follows: 1,3,5-benzenetricarboxylic acid and Cu(NO$_3$)$_2$·3H$_2$O are weighed with an analytical balance and poured into a beaker; distilled water, absolute ethanol, and a dimethylformamide solution are added into the above solution, stirring is performed to completely dissolve the 1,3,5-benzenetricarboxylic acid and Cu(NO$_3$)$_2$·3H$_2$O; the stirring bar is taken out, and the above dissolved reacting solution is poured into a bottle made of polytetrafluoroethylene to be crystallized; after the reaction is finished, and the bottle made of polytetrafluoroethylene is naturally cooled, washing and drying are carried out to obtain a dark blue powder; the dark blue powder obtained above is transferred to an Erlenmeyer flask for purification, suction filtration, washing, drying, and activation to obtain a final product, i.e., the dark blue solid powder Cu-MOF.

The specific preparation process of Cu/Mn-MOF and Cu/Fe-MOF is as follows: an appropriate amount of 1,3,5-benzenetricarboxylic acid and Cu(NO$_3$)$_2$·3H$_2$O are weighed and poured into a beaker; followed by adding distilled water, absolute ethanol, and a dimethylformamide solution, and stirring is performed to completely dissolve the 1,3,5-benzenetricarboxylic acid and Cu(NO$_3$)$_2$·3H$_2$O; appropriate amounts of Mn(NO)$_3$·4H$_2$O and FeCl$_3$·6H$_2$O are weighed with an analytical balance, dissolved in an appropriate amount of distilled water, and then slowly added into the solution obtained in the previous step, the reaction solution is poured into a bottle made of polytetrafluoroethylene for reacing for a certain period of time, naturally cooled, washed, and dried to obtain final products of Cu/Mn-MOF and Cu/Fe-MOF, respectively.

Mn-MOF is prepared by a solvothermal method. 1.62 mmol of $Mn(NO)_3·4H_2O$ is dissolved in 14 mL of DMF, stirred until dissolved, and then 0.85 mmol of trimesic acid is added, stirred vigorously at room temperature, and the mixture is transferred into a reaction kettle made of polytetrafluoroethylene for reacting at 150° C. for 6 hours. After cooling to room temperature, the reaction product is washed with DMF and dried at 60° C. to obtain the Mn-MOF.

Cr-MOF is a metal-organic framework material having an Lavoisier's structure, which is composed of a metal center $Cr^{3+}$ and an organic ligand trimesic acid ($H_3BTC$). The Cr-MOF material used in this experiment is synthesized by a solvothermal method according to literature. The specific steps for synthesizing the material are as follows: Cr powder is weighed by an analytical balance and poured into a lining of a reaction kettle made of polytetrafluoroethylene; distilled water and hydrogen fluoride (HF) are added to the lining of the reaction kettle, and stirred to dissolve the Cr powder; after the Cr powder is dissolved, $H_3BTC$ and the distilled water are added to the reaction system, stirred uniformly, and put into the reaction kettle after the stirring bar is taken out; the reaction kettle is placed in a drying oven with constant temperature for reacting; after the reaction is completed, and the reaction kettle is naturally cooled, suction filtration, purification, and washing to obtain the final solid product Cr-MOF.

The preparation methods of Cr/Fe-MOF, Cr/Cu-MOF and Cr/Mn-MOF are similar. 12 mmol of terephthalic acid is added to 20 mL of distilled water, and 11.4 mmol of chromium nitrate nonahydrate and 0.6 mmol of $FeCl_3·6H_2O$ are dissolved in 20 mL of distilled water, respectively. The above solutions are transferred to a hydrothermal synthesis reaction kettle, 0.6 mL of HF is added and stirred uniformly. The reaction kettle is sealed and placed in a dryer of 210° C. for 6 hours. The product obtained is recorded as Cr/Fe-MOF. The $FeCl_3·6H_2O$ is replaced by $Cu(NO_3)_2·3H_2O$ and $Mn(NO_3)_3·4H_2O$, respectively, and the products Cr/Cu-MOF and Cr/Mn-MOF are obtained according to the above steps.

Embodiment 1 1.0 mL of p-xylene (about 8 mmol) was added to a 100 mL round bottom flask, Cu-MOF (0.30 g), acetonitrile (20 mL), and hydrogen peroxide (30%, 2.0 mL, density 1.111 g/mL, 65 mmol) were successively added, after reacting at 30° C. for 5 hours, the reaction was stopped, and cooling, filtration and column chromatography were performed to obtain 1.06 g of 4-(Hydroxymethyl)benzoic acid (a yield of the column chromatography was about 96%, and the major by-product was 4-methylbenzoic acid).

Steps of the column chromatography in embodiment 1 were as follows: (1) a silica gel column is filled with normal phase silica gel, and then a filtrate was stirred with an appropriate amount of the normal phase silica gel and the filtrate was repeatedly adsorbed on the silica gel; (2) washing was performed with petroleum ether, a fraction was collected, and a solvent was distilled to obtain p-xylene; (3) washing was performed with a mixture of petroleum ether and methanol having a ratio of 1:1, a fraction was collected, and the solvent was distilled to obtain 4-methylbenzoic acid; (4) washing was performed with methanol, a fraction was collected, and the solvent was distilled to obtain 4-(Hydroxymethyl)benzoic acid. Column chromatography in other embodiments was similar.

Figure 3:
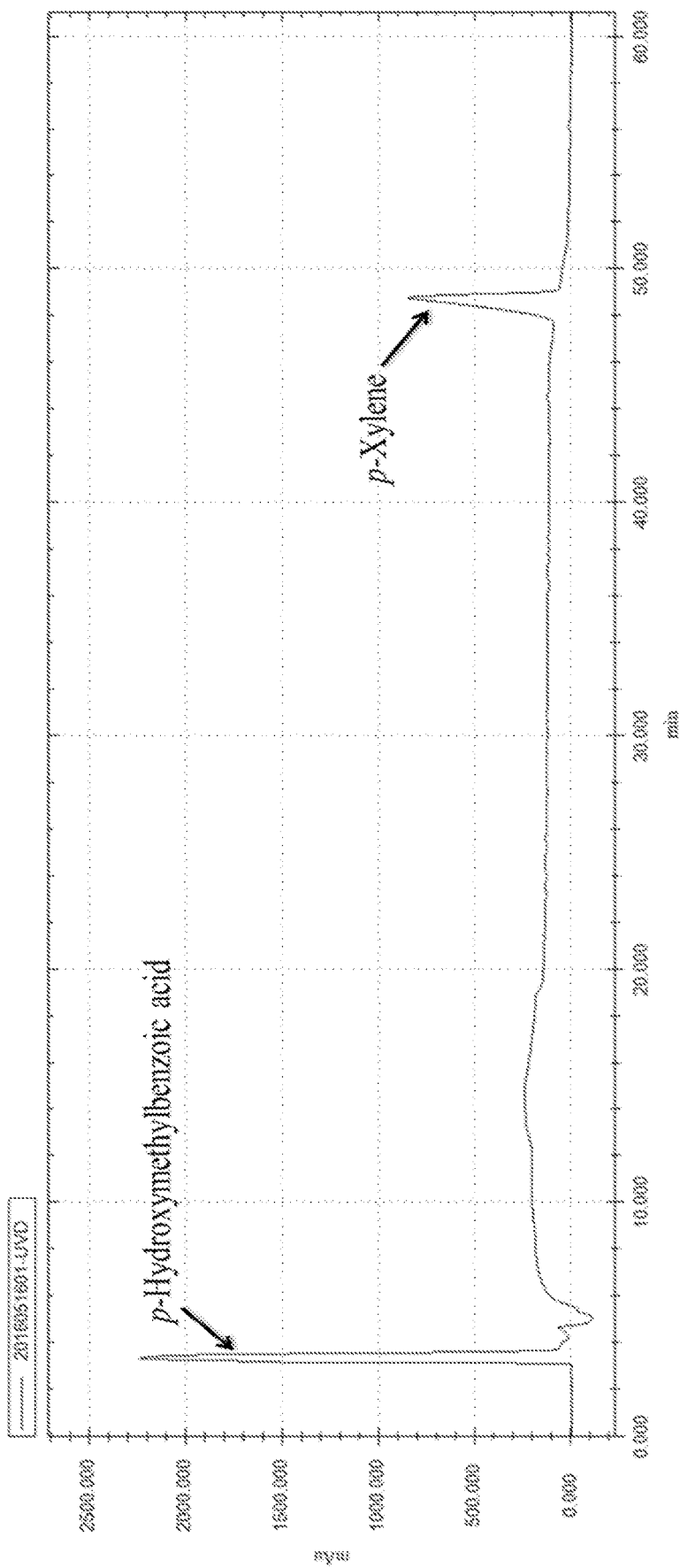
FIG. 3 shows an HPLC chromatogram of 4-(Hydroxymethyl)benzoic acid.
Figure 4:
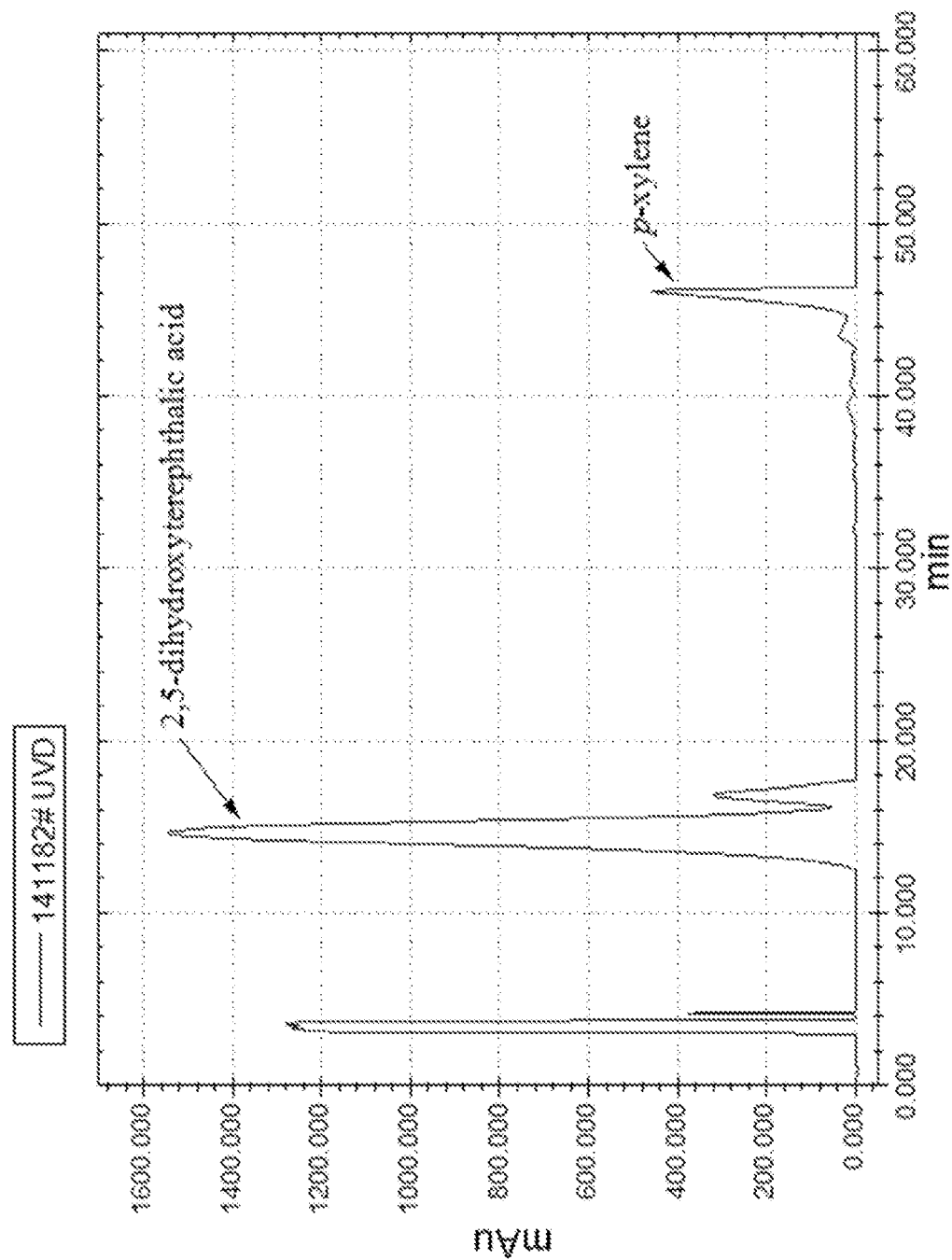
FIG. 4 shows an HPLC chromatogram of 2,5-dihydroxyterephthalic acid.
Figure 5A:
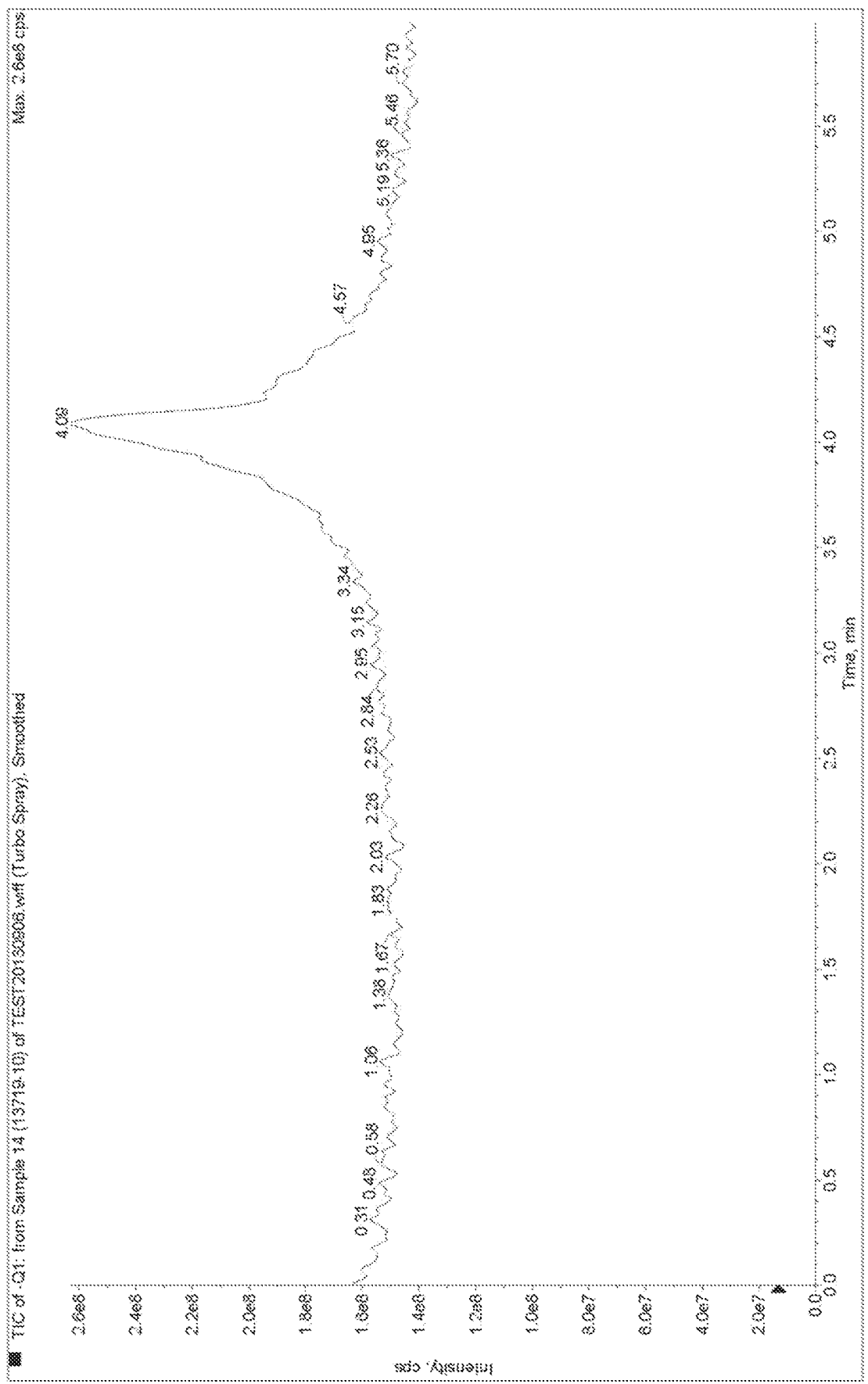
FIG. 5A and FIG. 5B show a liquid chromatography-tandem mass spectrometry (LC-MS-MS) of 2,5-dihydroxyterephthalic acid.
Figure 5B:
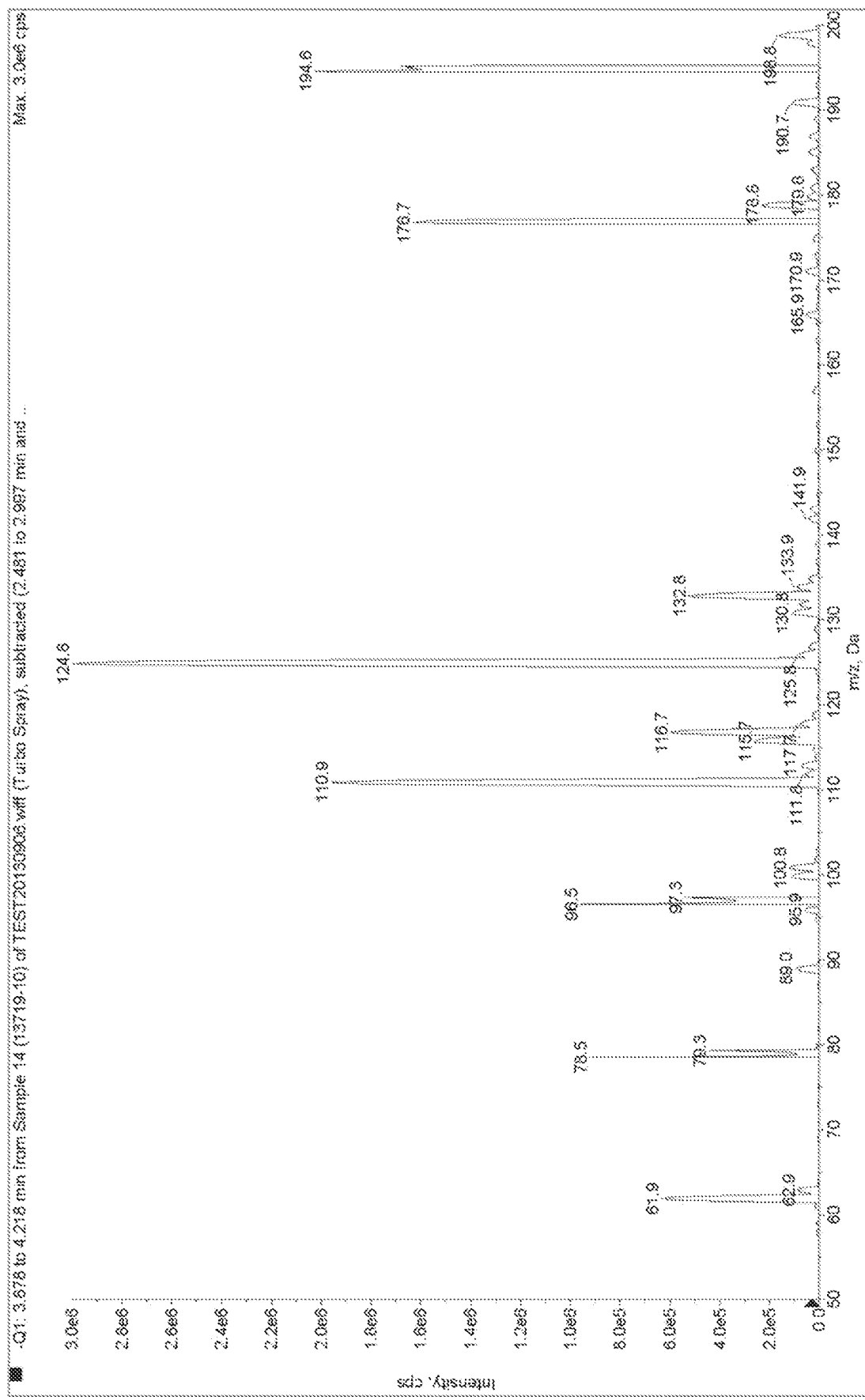

The 4-(Hydroxymethyl)benzoic acid described in embodiment 1 was verified by comparing with a standard product, and reactants and products were detected and monitored by high-performance liquid chromatography (HPLC) (The HPLC chromatogram was shown in FIG. 3).

Embodiment 2 1.0 mL of p-xylene (about 8 mmol) was added to a 100 mL round bottom flask, Cr-MOF (0.30 g), acetonitrile (30 mL), and hydrogen peroxide (30%, 2.0 mL, density 1.111 g/mL, 65 mmol) were successively added, after reacting at 30° C. for 3 hours, the reaction was stopped, cooling, filtration and column chromatogram were performed to obtain 0.86 g of 4-(Hydroxymethyl)benzoic acid (a yield of the column chromatogram was about 78%, and major by-products were p-methylbenzyl alcohol and 4-methylbenzoic acid).

Embodiment 3 1.0 mL of p-xylene (about 8 mmol) was added to a 100 mL round bottom flask, Mn-MOF (0.30 g), acetonitrile (20 mL), and hydrogen peroxide (30%, 2.0 mL, density 1.111 g/mL, 65 mmol) were successively added, after reacting at 30° C. for 5 hours, the reaction was stopped, cooling, filtration and column chromatogram were performed to obtain 0.73 g of 4-(Hydroxymethyl)benzoic acid (a yield of the column chromatogram was about 66%, and a major by-product was p-methylbenzyl alcohol).

Embodiment 4 1.0 mL of p-xylene (about 8 mmol) was added to a 100 mL round bottom flask, Cu-MOF (0.30 g), acetic acid (10 mL), and hydrogen peroxide (30%, 2.0 mL, density 1.111 g/mL, 65 mmol) were successively added, after reacting at 30° C. for 5 hours, the reaction was stopped, and cooling, filtration and column chromatogram were performed to obtain 0.55 g of 4-(Hydroxymethyl)benzoic acid (a yield of the column chromatogram was about 50%, and a major by-product was 4-methylbenzoic acid).

Embodiment 5 1.0 mL of p-xylene (about 8 mmol) was added to a 100 mL round bottom flask, Cu/Fe-MOF (0.20 g), acetonitrile (10 mL), and hydrogen peroxide (30%, 2.0 mL, density 1.111 g/mL, 65 mmol) were successively added, after reacting at 10° C. for 5 hours, the reaction was stopped, and cooling, filtration and column chromatogram were performed to obtain 0.72 g of 4-(Hydroxymethyl)benzoic acid (a yield of the column chromatogram was about 65%, and a major by-product was p-methylbenzyl alcohol).

Embodiment 6 1.0 mL of p-xylene (about 8 mmol) was added to a 100 mL round bottom flask, Cu/Mn-MOF (0.40 g), acetic acid (5 mL), acetonitrile (5 mL), and hydrogen peroxide (30%, 2.0 mL, density 1.111 g/mL, 65 mmol) were successively added, after reacting at 100° C. for 5 hours, the reaction was stopped, and cooling, filtration and column chromatogram were performed to obtain 1.01 g of 4-(Hydroxymethyl)benzoic acid (a yield of the column chromatogram was about 92%, and a major by-product was 4-methylbenzoic acid.).

Embodiment 7 1.0 mL of p-xylene (about 8 mmol) was added to a 100 mL round bottom flask, Cu/Mn-MOF (0.40 g), acetic acid (5 mL), acetonitrile (5 mL), and hydrogen peroxide (30%, 2.0 mL, density 1.111 g/mL, 65 mmol) were successively added, after reacting at 50° C. for 24 hours, the reaction was stopped, and cooling, filtration and column chromatogram were performed to obtain 1.03 g of 4-(Hydroxymethyl)benzoic acid (a yield of the column chromatogram was about 94%, and major by-products were p-methylbenzoic acid and terephthalic acid).

Embodiment 8 1.0 mL of p-xylene (about 8 mmol) was added to a 100 mL round bottom flask, Fe-MOF (0.30 g), acetic acid (20 mL), and hydrogen peroxide (30%, 2.0 mL, density 1.111 g/mL, 65 mmol) were successively added, after reacting at 70° C. for 5 hours, the reaction was stopped, and cooling, filtration and column chromatogram were performed to obtain 0.68 g of 4-(Hydroxymethyl)benzoic acid (a yield of the column chromatogram was about 62%, and a major by-product was terephthalic acid).

Embodiment 9 1.0 mL of p-xylene (about 8 mmol) was added to a 100 mL round bottom flask, Cu-MOF (0.50 g), ethanol (50 mL), hydrogen peroxide (30%, 2.0 mL, density 1.111 g/mL, 65 mmol) were successively added, after reacting at 70° C. for 1 hour, the reaction was stopped, and cooling, filtration and column chromatogram were performed to obtain 0.70 g of 4-(Hydroxymethyl)benzoic acid (a yield of the column chromatogram was about 64%, and a major by-product was p-methylbenzyl alcohol).

Embodiment 10 1.0 mL of p-xylene (about 8 mmol) was added to a 100 mL round bottom flask, Cr/Fe-MOF (0.50 g), and ethanol (20 mL) were successively added, and $N_2O$ (50 mL/min) was continuously introduced, after reacting at 70° C. for 1 hour, the reaction was stopped, and cooling, filtration and column chromatogram were performed to obtain 0.29 g of 4-(Hydroxymethyl)benzoic acid (a yield of the column chromatogram was about 26%, and major by-products were p-methylbenzyl alcohol, 4-methylbenzoic acid and terephthalic acid).

Embodiment 11 1.0 mL of p-xylene (about 8 mmol) was added to a 100 mL round bottom flask, Cu-MOF (0.50 g), and acetone (20 mL) were successively added, and $O_3$ (60 mL/min) was continuously introduced, after reacting at 50° C. for 2 hours, the reaction was stopped, and cooling, filtration and column chromatogram were performed to obtain 0.88 g of 4-(Hydroxymethyl)benzoic acid (a yield of the column chromatogram was about 80%, and major by-products were 4-methylbenzoic acid and terephthalic acid).

Embodiment 12 1.0 mL of p-xylene (about 8 mmol) was added to a 100 mL round bottom flask, Mn/Fe-MOF (0.40 g), acetone (20 mL), and t-butyl hydroperoxide (3 mL) were successively added, after reacting at 50° C. for 2 hours, the reaction was stopped, and cooling, filtration and column chromatogram were performed to obtain 0.90 g of 4-(Hydroxymethyl)benzoic acid (a yield of the column chromatogram was about 82%, and a major by-product was 4-methylbenzoic acid).

While pointing out the preferred implementations of the present invention, the above embodiments are presented as illustrations only and are not intended to limit the scope of the claims. The essential features of the present invention are can be clearly understood through the foregoing discussions and the embodiments, and the present invention may be modified to meet various applications and conditions without departing from the spirit and scope of the present invention.

What is claimed is:

1. A method for synthesizing 4-(Hydroxymethyl)benzoic acid using p-xylene (PX) as a raw material, comprising the following steps:
   dissolving the PX in an organic solvent to undergo an oxidation reaction with an oxidizing agent under an action of a transition metal modified metal-organic framework (M-MOF) catalyst to obtain a reacted product; and
   after the oxidation reaction, performing a post-treatment on the reacted product to obtain the 4-(Hydroxymethyl) benzoic acid;
   wherein, a metal element in the M-MOF catalyst is one selected from the group consisting of Fe, Cu, Cr, Mn, a mixture of Cu and Fe, a mixture of Cu and Cr, a mixture of Cu and Mn, a mixture of Fe and Mn, a mixture of Cr and Fe, and a mixture of Cr and Mn.

2. The method for synthesizing the 4-(Hydroxymethyl) benzoic acid using the PX as the raw material of claim 1, wherein, the organic solvent is at least one selected from the group consisting of methanol, ethanol, acetonitrile, acetone, acetic acid, ethyl acetate, and cyclohexane.

3. The method for synthesizing the 4-(Hydroxymethyl) benzoic acid using the PX as the raw material of claim 1, wherein, the organic solvent is at least one selected from the group consisting of acetonitrile, acetone, and acetic acid.

4. The method for synthesizing the 4-(Hydroxymethyl) benzoic acid using the PX as the raw material of claim 1, wherein, the oxidizing agent is at least one selected from the group consisting of $O_2$, air, hydrogen peroxide, $KHSO_5$, t-butyl hydroperoxide, $O_3$ and $N_2O$.

5. The method for synthesizing the 4-(Hydroxymethyl) benzoic acid using the PX as the raw material of claim 1, wherein, the oxidizing agent is at least one selected from the group consisting of 20%-40% hydrogen peroxide, t-butyl hydroperoxide, $O_3$ and $N_2O$.

6. The method for synthesizing the 4-(Hydroxymethyl) benzoic acid using the PX as the raw material of claim 1, wherein, the oxidizing agent is 20%-40% hydrogen peroxide and/or t-butyl hydroperoxide, and a molar ratio of the PX to the oxidizing agent is 1:(3-10).

7. The method for synthesizing the 4-(Hydroxymethyl) benzoic acid using the PX as the raw material of claim 1, wherein, a volume ratio of the PX to the organic solvent is 1:(1-100).

8. The method for synthesizing the 4-(Hydroxymethyl) benzoic acid using the PX as the raw material of claim 1, wherein, in the oxidation reaction, a reaction temperature is 10° C.-120° C.

9. The method for synthesizing the 4-(Hydroxymethyl) benzoic acid using the PX as the raw material of claim 1, wherein, a mass ratio of the PX to the M-MOF catalyst is 1:(1.5-3).

10. The method for synthesizing the 4-(Hydroxymethyl) benzoic acid using the PX as the raw material of claim 1, wherein, a mass ratio of the metal element to a MOF carrier in the M-MOF catalyst is 1:(10-100).

11. The method for synthesizing the 4-(Hydroxymethyl) benzoic acid using the PX as the raw material of claim 2, wherein, a mass ratio of the metal element to a MOF carrier in the M-MOF catalyst is 1:(10-100).

12. The method for synthesizing the 4-(Hydroxymethyl) benzoic acid using the PX as the raw material of claim 3, wherein, a mass ratio of the metal element to a MOF carrier in the M-MOF catalyst is 1:(10-100).

13. The method for synthesizing the 4-(Hydroxymethyl) benzoic acid using the PX as the raw material of claim 4, wherein, a mass ratio of the metal element to a MOF carrier in the M-MOF catalyst is 1:(10-100).

14. The method for synthesizing the 4-(Hydroxymethyl) benzoic acid using the PX as the raw material of claim 5, wherein, a mass ratio of the metal element to a MOF carrier in the M-MOF catalyst is 1:(10-100).

15. The method for synthesizing the 4-(Hydroxymethyl) benzoic acid using the PX as the raw material of claim 6, wherein, a mass ratio of the metal element to a MOF carrier in the M-MOF catalyst is 1:(10-100).

16. The method for synthesizing the 4-(Hydroxymethyl) benzoic acid using the PX as the raw material of claim 7, wherein, a mass ratio of the metal element to a MOF carrier in the M-MOF catalyst is 1:(10-100).

17. The method for synthesizing the 4-(Hydroxymethyl) benzoic acid using the PX as the raw material of claim 8, wherein, a mass ratio of the metal element to a MOF carrier in the M-MOF catalyst is 1:(10-100).

18. The method for synthesizing the 4-(Hydroxymethyl) benzoic acid using the PX as the raw material of claim 9, wherein, a mass ratio of the metal element to a MOF carrier in the M-MOF catalyst is 1:(10-100).

* * * * *